United States Patent
Suzuki et al.

(10) Patent No.: US 6,803,444 B2
(45) Date of Patent: Oct. 12, 2004

(54) POLYHYDROXYALKANOATE POLYESTER HAVING VINYL PHENYL STRUCTURE IN THE SIDE CHAIN AND ITS PRODUCTION METHOD

(75) Inventors: Tomohiro Suzuki, Kanagawa (JP); Etsuko Sugawa, Kanagawa (JP); Tetsuya Yano, Kanagawa (JP); Tsuyoshi Nomoto, Tokyo (JP); Takeshi Imamura, Kanagawa (JP); Tsutomu Honma, Kanagawa (JP); Takashi Kenmoku, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 208 days.

(21) Appl. No.: 10/084,167

(22) Filed: Feb. 28, 2002

(65) Prior Publication Data

US 2003/0059907 A1 Mar. 27, 2003

(30) Foreign Application Priority Data

Feb. 28, 2001 (JP) ........................................ 2001-055304
Feb. 26, 2002 (JP) ........................................ 2002-049638

(51) Int. Cl.$^7$ .............................. C08G 63/06; C12P 7/62

(52) U.S. Cl. ........................ 528/361; 525/450; 525/451; 524/732; 524/734; 524/770; 524/773; 435/135; 435/146; 435/253.3; 435/255.1; 435/874; 435/877

(58) Field of Search .......................... 528/361; 525/450, 525/451; 524/732, 734, 770, 773; 435/135, 146, 253.3, 255.1, 874, 877

(56) References Cited

U.S. PATENT DOCUMENTS 6,645,743 B1 * 11/2003 Honma et al. .............. 435/146

FOREIGN PATENT DOCUMENTS

JP 2989175 12/1999
JP 2001-28856 1/2001

OTHER PUBLICATIONS

Curley, J.M., et al., "Production of Poly(3–hydroxyalkanoates) Containing Aromatic Substituents by *Pseudomonas oleovorans*", Macromolecules, vol. 29, No. 5, pp. 1726–1766 (1996).

Fritzsche, et al.; "An unusual bacterial polyester with a phenyl pendant group"; Makromol. Chem., 191, 1957–1965 (1990).

Ritter, et al.; "Bacterial production of polyesters bearing phenoxy groups in the side chains, 1"; Macromol. Chem. Phys. 195, 1665–1672 (1994).

de Koning, et al.; "A biodegradable rubber by crosslinking poly(hydroxyalkanoate) from *Pseudomonas oleovorans*"; Polymer, 35, 10, 2090–2097 (1994).

Curley, et al; "Production of Poly(3–hydroxyalkanoates) Containing Aromatic Substituents by *Pseudomonas oleovorans*"; Macromol. 29, 1762–1766 (1996).

Kim, et al.; "Preparation and Characterization of Poly(β–hydroxyalkanoates) Obtained from *Pseudomonas olevorans* Grown with Mixtures of 5–Phenylvaleric Acid and n–Alkanoic Acids" Macromol. 24, 5256–5260 (1991).

Gross, et al.; "Cyanophenoxy–Containing Microbial Polyesters: Structural Analysis, Thermal Properties, Second Harmonic Generation and In–Vivo Biodegradability" Polym. Int'l. 39, 3, 205–213 (1996).

Lee, et al.; "Crosslinking of microbial copolyesters with pendent epoxide groups by diamine"; Polymer 40, 3797–3793 (1999).

(List continued on next page.)

*Primary Examiner*—Samuel A. Acquah
(74) *Attorney, Agent, or Firm*—Fitzpatrick, Cella, Harper & Scinto

(57) ABSTRACT

Polyhydroxyalkanoate type polyester that comprises one unit % or more of 3-hydroxy-ω-(4-vinylphenyl)alkanoic acid units. A microbial production method is also provided.

20 Claims, 1 Drawing Sheet

OTHER PUBLICATIONS

Aróstegui; "Bacterial Polyesters Produced by *Pseudomonas oleovorans* Containing Nitrophenyl Groups"; Macromol., 32, 9, 2987–2895 (1999).

Lee, et al.; "Hydrophilic bacterial polyesters modified with pendant hydroxyl groups"; Polymer 41, 1703–1709 (1999).

* cited by examiner

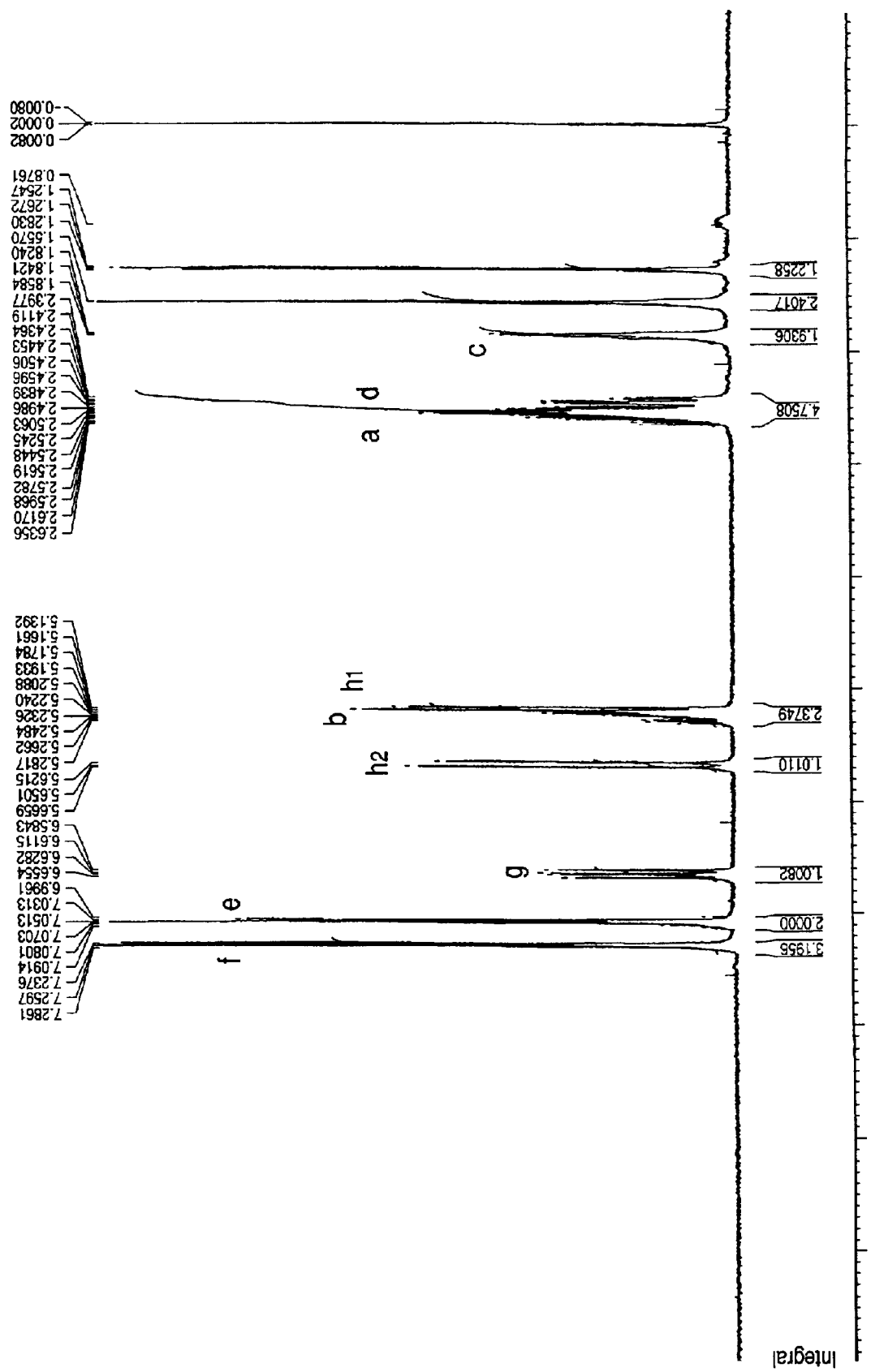

POLYHYDROXYALKANOATE POLYESTER HAVING VINYL PHENYL STRUCTURE IN THE SIDE CHAIN AND ITS PRODUCTION METHOD

BACKGROUND OF THE INVENTION

1. Field of the Invention

The present invention relates to a polyester of polyhydroxyalkanoate (PHA) type that comprises a novel unit and to a production method thereof utilizing a microorganism. More specifically, it relates to a PHA polyester that comprises a 3-hydroxy-ω-(4-vinylphenyl)alkanoic acid unit and to a production method of such a PHA utilizing a microorganism that can produce the PHA using ω-(4-vinylphenyl) alkanoic acid as a raw material.

2. Related Background Art

So far, it is known that a large number of microorganisms produce poly-3-hydroxybutyrate (PHB) or other PHAs and accumulate them within the cell ("Biodegradable Plastics Handbook", edited by Biodegradable Plastics Society, published by N.T.S. Co., Ltd., p.178–197 (1995)). These microbial polymers such as PHA can be used for producing various products by the melting process just as conventional plastics. Further, microbial polymers such as PHA have biodegradability which provides an advantage that they are completely decomposed by microorganisms in nature. Thus, for example, unlike conventional synthetic polymer compounds, discarded microbial PHA would not remain as it is in the natural environment or would not cause pollution. Further, microbial PHA generally has good biocompatibility and its application to a medical soft member is expected.

It is also known that the composition and constitution of microbial PHA varies depending to the microorganism used for production, culture medium composition, culturing conditions and the like. So far, mainly in order to improve physical properties of PHA, studies to control the composition and structure of microbial PHA have been conducted.

As part of studies to control the composition and structure of microbial PHA, recently various studies have been carried out in order to make microorganisms produce PHA having an aromatic ring on the unit.

There are reports that *Pseudomonas oleovorans* produces PHA comprised of 3-hydroxy-5-phenylvaleric acid units using 5-phenylvaleric acid as a substrate (Makromol. Chem., 191, 1957–1965 (1990) and Macromolecules, 24, 5256–5260 (1991)).

In Macromolecules, 29, 1762–1766 (1996), it is reported that using 5-(p-tolyl)valeric acid as a substrate, *Pseudomonas oleovorans* produces PHA comprised of 3-hydroxy-5-(p-tolyl)valeric acid units.

In Macromolecules, 32, 2889–2895 (1999), it is reported that using 5-(2,4-dinitrophenyl)valeric acid as a substrate, *Pseudomonas oleovorans* produces PHA containing 3-hydroxy-5-(2,4-dinitrophenyl)valeric acid units and 3-hydroxy-5-(p-nitrophenyl)valeric acid units.

In Macromol. Chem. Phys., 195, 1665–1672 (1994), it is reported that using 11-phenoxyundecanoic acid as a substrate, *Pseudomonas oleovorans* produces PHA copolymer containing 3-hydroxy-5-phenoxyvaleric acid units and 3-hydroxy-9-phenoxynonanoic acid units.

Japanese Patent Publication No. 2989175 discloses a homopolymer comprised of 3-hydroxy-5-(monofluoro phenoxy)pentanoate (3H5 (MFP)P) units or 3-hydroxy-5-(difluoro phenoxy)pentanoate (3H5 (DFP) P) units; a copolymer containing at least 3H5 (MFP)P units or 3H5 (DFP)P units; *Pseudomonas putida* having an ability to produce these polymers; and a production method thereof using Pseudomonas species. It also discloses that the microorganism can produce polymers having phenoxy groups substituted with one or two fluorine atoms at the end of the side chains by assimilating long chain fatty acids having such a substituted phenoxy group, and as the advantage of the invention, it is written that such a polymer has a high melting point and good workability, further providing stereoregularity and water repellency.

Also, other than the fluorine substituted PHA having fluorine atoms on the aromatic ring in the unit, PHAs having cyano and/or nitro substituents on the aromatic ring in the unit have been studied.

Can. J. Microbiol., 41, 32–43 (1995) and Polymer International, 39, 205–213 (1996) report that PHA containing 3-hydroxy-6-(p-cyanophenoxy)hexanoic acid or 3-hydroxy-6-(p-nitrophenoxy)hexanoic acid as a monomer unit is yielded by *Pseudomonas oleovorans* ATCC 29347 or *Pseudomonas putida* KT 2442 using octanoic acid and 6-(p-cyanophenoxy)hexanoic acid or 6-(p-nitrophenoxy) hexanoic acid as the substrates.

PHA containing such a unit having a substituted aromatic ring is a multifunctional PHA because it has functions due to the substituents of the aromatic rings and properties such as a high melting point and good workability due to the aromatic rings.

On the other hand, studies have been vigorously carried out to obtain multifunctional PHA by introducing desired functional groups to the side chains of PHA polymer having a vinyl group in the unit through chemical conversion utilizing the vinyl groups.

Polymer, 41, 1703–1709 (2000) reports that a polyester having a vinyl group on the side chains was yielded by a Pseudomonas and then the vinyl groups were oxidized to produce a polyester having a hydroxyl group on the side chains.

Macromolecules, 31, 1480–1486 (1998) reports that polyester having vinyl groups on the side chains was yielded by *Pseudomonas oleovorans* and then the vinyl groups were epoxidized to produce a polyester having an epoxy group on the side chains.

Polymer, 40, 3787–3793 (1999) reports analysis of the crosslinking reaction and products when a polymer that has an epoxy group on the side chains and was produced by a similar method was heated with hexamethylenediamine.

Further, Polymer, 35, 2090–2097 (1994) reports that physical properties of polyester were improved by crosslinking reaction within the polyester molecule using vinyl groups on the side chains of the polyester.

As seen from above studies, vinyl group, being an unsaturated hydrocarbon group, is highly reactive in addition reaction etc., so that vinyl group can be used to introduce various functional groups and to carry out chemical conversion. Further, a vinyl group can be a foothold or a crosslinking point in the polymer crosslinking reaction. Consequently, in view of PHA application as a functional material, it is very useful to have a vinyl group in the unit that constitutes PHA.

All of known polyester polymers having vinyl groups have a structure where vinyl groups are born at the end of alkyl side chains directly bonded to the skeletal structure of the polyester. However, polyesters having alkyl side chains generally do not have so high glass transition temperature and melting point and its thermal characteristics are not always favorable in melt-processing, and there are not many materials having excellent properties as film or processed goods. On the other hand, polyester having an aromatic ring in the side chain, as already described, has generally a high melting point and good workability.

Accordingly, it is desirable to use polyester having aromatic rings and vinyl groups together on the side chains to develop new functional polymers having excellent processing properties. So far, there is no report indicating that an aromatic ring and a functional group such as the vinyl group were introduced in a side chain of polyester.

The present invention is to solve the above described problem, and an object of the present invention is to provide polyester having an aromatic ring and a vinyl group on the side chain, especially PHA polyester having biodegradability and its production method. More specifically, the present invention provides a PHA polyester having an aromatic ring having a vinyl substituent on the ring on a side chain and a production method thereof using a microorganism.

SUMMARY OF THE INVENTION

The present inventors concentrated on the study to achieve the above-described object, and accomplished the present invention described in the following.

According to an aspect of the present invention there is provided a polyhydroxyalkanoate type polyester comprising one unit % or more of 3-hydroxy-ω-(4-vinylphenyl)alkanoic acid unit represented by chemical formula (1):

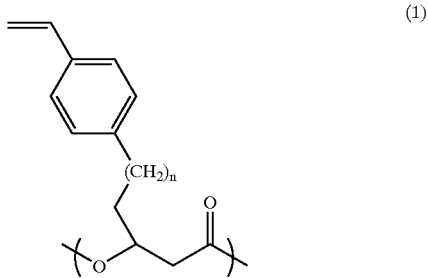

$n = 0–7$ where n is one or more integers arbitrarily selected from 0 to 7.

Polyester in the present invention, if circumstances require, may contain 3-hydroxy alkanoic acid units shown by the following chemical formula (2) in addition to the above 3-hydroxy-ω-(4-vinylphenyl)alkanoic acid unit.

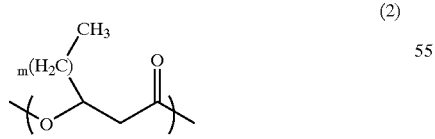

$m = 0–8$ (m is one or more integers arbitrarily selected from the range shown in the formula.)

An example of such a polyester includes polyester containing one unit % of more of 3-hydroxy-5-(4-vinylphenyl) valeric acid units shown by the following chemical formula (3) in the molecule.

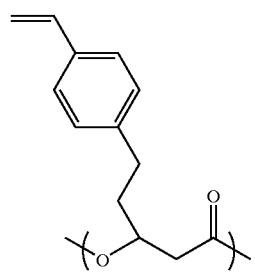

According to another aspect of the present invention, there is provided a method of producing the above-described PHA polyester comprising the steps of:

(1) providing ω-(4-vinylphenyl)alkanoic acid represented by chemical formula (4) as a raw material,

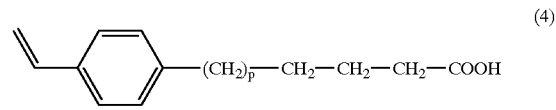

$p = 0–7$ where p is one or more integers arbitrarily selected from 0 to 7; and (2) producing a polyester comprising one unit % or more of 3-hydroxy-ω-(4-vinylphenyl)alkanoic acid unit represented by chemical formula (1) by using a microorganism capable of producing the polyester from the ω-(4-vinylphenyl)alkanoic acid;

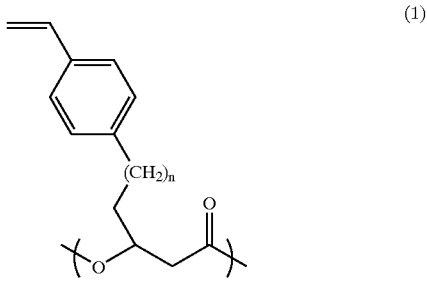

$n = 0–7$ where n is one or more integers arbitrarily selected from 0 to 7.

BRIEF DESCRIPTION OF THE DRAWINGS

FIGURE shows 1H-NMR spectrum of PHA polymer obtained in Example 1.

DETAILED DESCRIPTION OF THE INVENTION

The present invention provides a polyester containing 3-hydroxy-ω-(4-vinylphenyl)alkanoic acid units shown by the following chemical formula (1) (hereinafter referred to as the PHA polyester of the invention), a novel PHA polyester having an aromatic ring substituted with a vinyl group in the side chain:

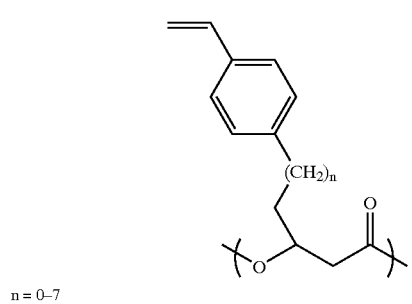

$n = 0-7$ (1)

(n is one or more integers arbitrarily selected from the range shown in the formula.). The PHA polyester of the invention can be produced by using a microorganism as described more specifically later.

This 3-hydroxy-ω-(4-vinylphenyl) alkanoic acid unit has a vinyl group at p-position of an aromatic phenyl group. Vinyl groups are highly reactive in addition reactions etc. and are subject to introduction of various functional groups and chemical conversion. Thus, the PHA polymer of the invention has not only processing properties such as a high melting point and good workability owing to the presence of phenyl groups, but also utility that a novel function can be provided by introducing various functional groups or by chemical conversion using vinyl groups.

Further, the PHA polyester of the invention may contain other units, usually, some 3-hydroxy alkanoic acid units. Preferably, the unit represented by chemical formula (1) is contained at least one unit % or more, usually as a main component, that is, at least 50 unit % or more, more preferably, 70 unit % or more in view of high melting point and good workability which depend on the ratio of phenyl group.

Specifically, when all of the other units in the PHA polyester of the invention are 3-hydroxy alkanoic acid represented by the chemical formula (2), the unit of chemical formula (1) is preferably contained 70% or more.

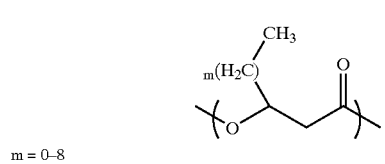

$m = 0-8$ (2)

(m is one or more integers arbitrarily selected from the range shown in the formula.)

However, when the PHA of the invention contains units having a phenyl group in the side chain in addition to the unit represented by chemical formula (1), the total of the similar units is preferably 70% or more. Depending on the use of the PHA of the invention or the purpose of utilizing the unit represented by chemical formula (1), such a high content may not always be required. However, when the content of the unit shown by the chemical formula (1) is less than one unit %, characteristics owing to the existence of the unit in the polymer will not be exhibited as a whole.

Preferably, 3-hydroxy alkanoic acid unit contained as the other constituent is a 3-hydroxy alkanoic acid unit shown by the above chemical formula (2) in which the side chain is a linear alkyl group of 1 to 9 carbons. Because 3-hydroxy alkanoic acid units of this type do not have high reactivity as the vinyl group, they would not cause unnecessary reaction allowing selective reaction of the vinyl group when various functional groups are introduced or chemical conversion is performed. By the way, the PHA of the invention is subjected to melt-molding and processed to various final products. Thus, if the molecular weight is excessively large, the melting point of the polyester exceeds the melting temperature range because of the excess action of the phenyl group to raise the melting temperature. Taking it in consideration, the number average molecular weight of the PHA of the invention is preferably in the range of 3000 to 200,000.

In the following, the method of producing the PHA polyester of the invention is described in detail. The PHA polyester of the invention can be produced as biodegradable PHA polyester by a microorganism. Specifically, ω-(4-vinylphenyl)alkanoic acid shown by the following chemical formula (4):

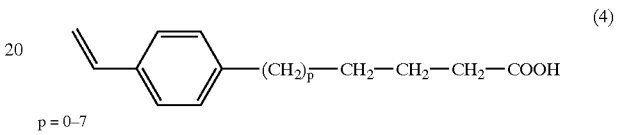

$p = 0-7$ (4)

(p is zero or an integer not less than 8) is converted to corresponding 3-hydroxy-ω-(4-vinylphenyl)alkanoic acid unit represented by chemical formula (1) by a PHA-producing microorganism. Then the microorganism produces and accumulates PHA polyester containing the converted units.

For example, when 5-(4-vinylphenyl)valeric acid represented by the following chemical formula (5) is used as a raw material,

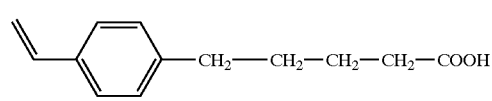

(5)

PHA polyester containing 3-hydroxy-5-(4-vinylphenyl) valeric acid unit represented by chemical formula (3) is produced and accumulated.

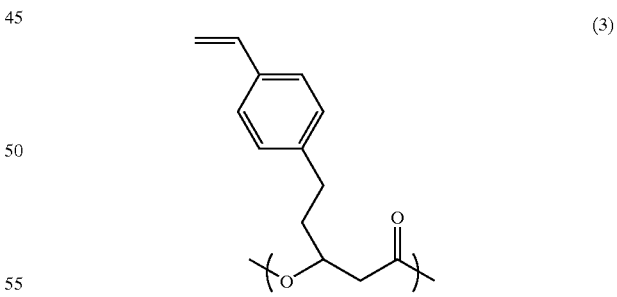

(3)

When 8-(4-vinylphenyl)octanoic acid represented by chemical formula (6) is used as a raw material,

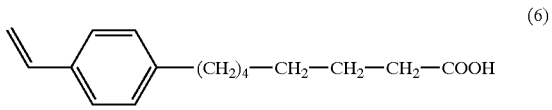

(6)

PHA polyester containing 3-hydroxy-8-(4-vinylphenyl) octanoic acid unit represented by chemical formula (7)

(7)

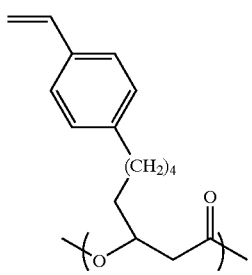

and 3-hydroxy-6-(4-vinylphenyl)hexanoic acid unit represented by chemical formula (8) is produced and accumulated.

(8)

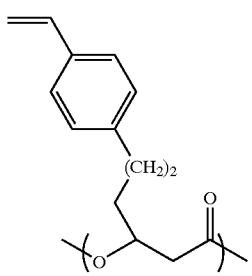

Further, when 10-(4-vinylphenyl)decanoic acid shown by the following chemical formula (9) is used as a raw material, (9)

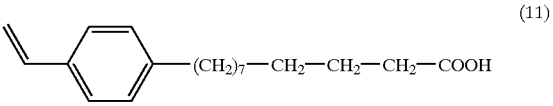

PHA polyester containing 3-hydroxy-10-(4-vinylphenyl) decanoic acid unit represented by chemical formula (10), (10)

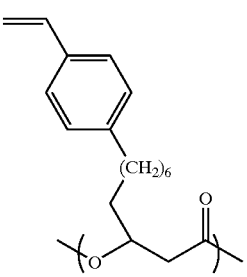

3-hydroxy-8-(4-vinylphenyl)octanoic acid unit represented by chemical formula (7), (7)

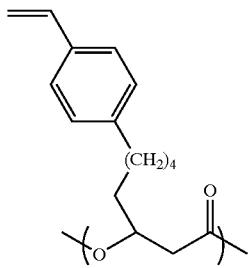

and 3-hydroxy-6-(4-vinylphenyl)hexanoic acid unit represented by chemical formula (8) is yielded and accumulated.

(8)

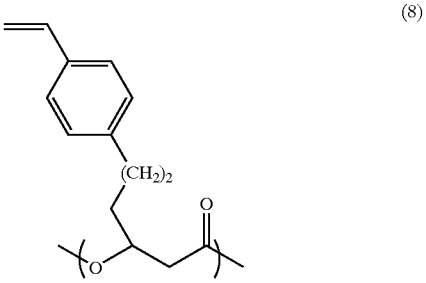

When 11-(4-vinylphenyl)undecanoic acid shown by the following chemical formula (11) is used as a raw material, (11)

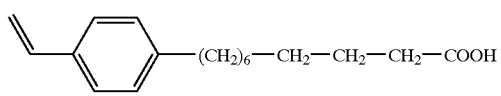

PHA polyester containing 3-hydroxy-9-(4-vinylphenyl) nonanoic acid unit represented by chemical formula (12), (12)

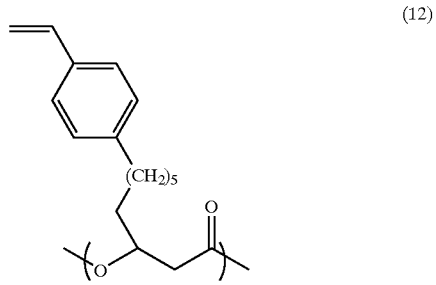

3-hydroxy-7-(4-vinylphenyl)heptanoic acid unit represented by chemical formula (13), (13)

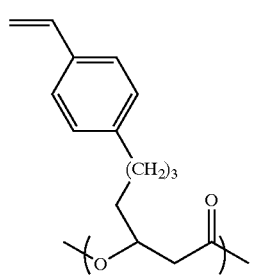

and 3-hydroxy-5-(4-vinylphenyl)valeric acid unit represented by chemical formula (3) is yielded and accumulated.

(3)

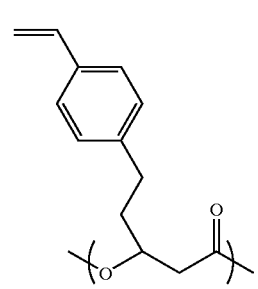

Generally, the produced PHA polyester has hydrophobic atomic groups such as 4-vinylphenyl group on the side chain of 3-hydroxy-ω-(4-vinylphenyl)alkanoic acid unit, so that the PHA polyester has poor water solubility and accumulated in the microbial cells. Thus, the polyester is easily separated from the culture medium by culturing the microorganism and collecting the cells accumulating the PHA polyester. After the collected cells are washed and dried, the objective PHA polyester can be recovered.

To recover the PHA polyester from the cultured microbial cells, any ordinary method can be used. For example, extraction with an organic solvent such as chloroform, dichloromethane and acetone is most convenient, but dioxane, tetrahydrofuran and acetonitrile may be used. If the condition would not favor the use of organic solvents, PHA can be recovered from the cells disrupted by using one of the following methods removing other cell components. The method includes: surfactant treatment such as SDS, enzyme treatment such as lysozyme, chemical treatment such as hypochlorite, ammonia and EDTA, ultrasonic disruption, homogenizer disruption, pressure disruption, bead impact disruption, grinding, pounding and freeze-and-thawing.

The microorganism used for the production of the PHA polyester of the present invention may be any microorganisms capable of producing PHA, particularly, a microorganism that can produce PHA polyester containing 3-hydroxy-ω-(4-vinylphenyl)alkanoic acid units represented by chemical formula (1) when cultured in a culture medium containing ω-(4-vinylphenyl)alkanoic acid (chemical formula (4)). An example of such a microorganism is of genus Pseudomonas. More specifically, it is preferable to use such strains as those capable of producing PHA, but exhibiting no enzyme activities to oxydize or epoxydize the vinyl substituent on the phenyl group. More preferable strains are exemplified by, for example, *Pseudomonas cichorii* YN2, FERM BP-7375, *Pseudomonas cichorii* H45, PERM BP-7374, *Pseudomonas jessenii* P161, FERM BP-7376, and *Pseudomonas putida* P91, PERM BP-7373.

These four microorganisms have been deposited in International Patent Organism Depositary (IPOD) of Institute of Advanced Industrial Science and Technology (AIST) (former Agency of Industrial Science and Technology of former Ministry of International Trade and Industry), and are described in Japanese patent Application Laid-Open No. 2001-288256.

Further, the components of the PHA polyester of the invention, 3-hydroxy-ω-(4-vinylphenyl)alkanoic acid unit represented by chemical formula (1) and 3-hydroxyalkanoic acid unit represented by chemical formula (2), both have asymmetric carbon atoms in their 3 positions. Thus, there exist stereoisomers of PHA differing in absolute configuration due to these asymmetric centers. In view of the biodegradability, PHAs of which units are all R-stereoisomer are most preferable.

According to the present invention, corresponding alkanoic acid is converted to 3-hydroxyalkanoic acid by a microorganism, so that the PHA polyester obtained by the production method of the present invention has a feature that all units are R-stereoisomers.

In the production method of the present invention where the PHA-producing microorganism is cultured in a culture medium containing a substrate, the culture conditions are preferably chosen as follows.

The concentration of a substrate for producing objective PHA polyester of the invention, i.e., ω-(4-vinylphenyl) alkanoic acid represented by chemical formula (4), in a culture medium is preferably in the range of 0.01% to 1% (w/v), more preferably in the range of 0.02% to 0.2% (w/v). Further, when the PHA polyester is to contain another type of 3-hydroxyalkanoic acid units in addition to 3-hydroxy-ω-(4-vinylphenyl)alkanoic acid units, corresponding 3-hydroxyalkanoic acid is added as a substrate in the culture medium.

The culture medium may contain nutrients such as yeast extract, polypeptone and meat extract to accelerate the microbial growth. That is, peptides in the form of yeast extract, polypeptone or meat extract can be added as an energy source and carbon source.

Alternatively, carbohydrates can be added to the culture medium as an energy and carbon source consumed by the growth of the microorganism. For example, aldose such as glyceraldehyde, erythrose, arabinose, xylose, glucose, galactose, mannose and fructose; alditol such as glycerol, erythritol and xylitol; aldonic acids such as gluconic acid; uronic acids such as glucuronic acid, galacturonic acid etc.; disaccharides such as maltose, sucrose and lactose and the like can be used.

It is also possible to replace the above described saccharides with organic acids, more specifically carboxylic acids those participating the TCA cycle, or those derived from the TCA cycle by a few biochemical steps. For example, hydroxycarboxylic acids or oxocarboxylic acids such as pyruvic acid, oxalacetic acid, citric acid, isocitric acid, ketoglutaric acid, succinic acid, fumaric acid, malic acid, lactic acid and others, or their water soluble salts can be used. Alternatively, amino acids, for example, amino acids such as aspartic acid and glutamic acid or salts thereof can be used. When organic acids or their salts are added to the culture medium, it is preferable to select one or more of pyruvic acid, oxalacetic acid, citric acid, isocitric acid, ketoglutaric acid, succinic acid, fumaric acid, malic acid, lactic acid and salts thereof. When amino acids or their salts are added to the culture medium, it is preferable to select one or more of aspartic acid, glutamic acid and their salts. In that case, it is possible to add all or part of them in the form of a water soluble salt to uniformly dissolve them in the culture medium without affecting pH, if necessary.

Any of above peptides, carbohydrates, organic acids and their salts and amino acids and their salts can be added singly or in combination to the culture medium as nutrients to enhance the growth of the microorganism. In that case, the amount to be added in the culture medium is usually in the range of 0.1% to 5% (w/v), more preferably in the range of 0.2% to 2% (w/v). When a salt of an organic acid is used, the addition amount is that of the corresponding organic acid. When two or more kinds are used together, it is desirable that the total amount is in the above described range.

Any inorganic culture media containing phosphate and a nitrogen source such as an ammonium salt or nitrate can be used as a basal salt medium in the present invention. Further, the productivity of PHA can be improved by controlling the concentration of a nitrogen source contained in the medium.

Any culture temperature can be used as long as the strain to be used can well proliferate at the temperature, but it is proper to select culture temperature ranging from 15° C. to 30° C. Any type of cultivation method, liquid or solid, can be used as long as it can hold substrates and nutrients, the microorganism to be used can grow in or on it, and it is in the form suitable for PHA production. Further, it may be batch culture, fed-batch culture, semicontinuous culture, or continuous culture. Suitable liquid batch culture methods include culture in a shaking flask to supply oxygen by shaking, or a jar fermenter culture where oxygen is supplied by the agitation-aeration system.

As a technique of microbial production of PHA, there is also a two-step culture method in addition to the above described one-step culture in which a microorganism is cultured in an inorganic salt medium containing the substrate at a predetermined amount, phosphate and a nitrogen source such as ammonium salt or nitrate. In the two-step culture, the microorganism is first fully grown in the above-described culture medium for the one-step culture and then transferred to and cultured in a secondary culture medium in which the nitrogen source such as ammonium chloride is limited but the substrate is contained at a predetermined concentration for PHA production and accumulation. By this two-step culture method, the PHA productivity may be improved.

The composition of M9 medium, an inorganic salt culture medium used in the following Examples, is shown below. This is an example of inorganic basal salt media that can be used in the production method of the present invention.

| Composition of M9 medium (g/l) | |
| --- | --- |
| $Na_2HPO_4$: | 6.3 |
| $KH_2PO_4$: | 3.0 |
| $NH_4Cl$: | 1.0 |
| NaCl: | 0.5, pH = 7.0 |

Furthermore, in order to obtain good growth and high PHA productivity, it is necessary to add a stock solution of trace elements of the following composition to the inorganic culture medium such as M9 medium to about 0.3% (v/v). The addition of such a minor constituent solution is to supply trace metal elements that are used in the growth of a microorganism.

Composition of a minor constituent solution (g/l) Nitrilotriacetic acid: 1.5;
$MgSO_4$: 3.0; $MnSO_4$: 0.5; NaCl: 1.0; $FeSO_4$: 0.1;
$CaCl_2$: 0.1; $CoCl_2$: 0.1; $ZnSO_4$: 0.1;
$CuSO_4$: 0.1; $AlK(SO_4)_2$: 0.1;
$H_3BO_3$: 0.1; $Na_2MoO_4$: 0.1; $NiCl_2$: 0.1

EXAMPLES

In the following, the present invention will be described more concretely by Examples. These Examples are the best mode of the invention, but the present invention should not be limited to them.

Example 1

Using M9 medium containing 5-(4-vinylphenyl)valeric acid and polypeptone as a peptide source (nutrient), strain YN2 was cultured by one-step culture for PHA production.

A colony of strain YN2 grown on an agar plate was inoculated in a 500 ml shaking flask containing 200 ml of M9 culture medium containing 0.5% of polypeptone and 0.05% of 5-(4-vinylphenyl)valeric acid and cultured at 30° C. for 48 hours. After that, the grown cells were collected by centrifugal separation and washed with methanol and lyophilized. The dry cell matter was weighed.

Chloroform was added to the dried cells to extract the polymer at 40° C. for 24 hours. The chloroform extract was filtered to remove cell debris and the chloroform layer in which the polymer had been dissolved was concentrated by an evaporator. Then the residue was recovered with cold methanol. The recovered precipitate was then dried under reduced pressure to obtain an objective polymer. The dry cell weight was 139 mg and the weight of the obtained (recovered) polymer was 22 mg.

The average molecular weight of the obtained polymer was measured by gel permeation chromatography (HLC-8220 GPC; Toso Co., Ltd., Column: TSK-GEL Super HM-H; Toso Co., Ltd., Solvent: chloroform, polystyrene standards). As a result, the obtained polymer had the number-average molecular weight of Mn=3700 and the weight-average molecular weight of Mw=8900.

The structure of the obtained polymer was determined by 1H-NMR (FT-NMR: Bruker DPX400; resonance frequency: 400 MHz; measurement nuclide: 1H; used solvent: CDC13; reference: capillary enclosed TMS/CDC13; measurement temperature: room temperature). The spectrum chart by 1H-NMR is shown in FIGURE. And the assignment of hydrogen atoms giving respective resonance signals in 1H-NMR spectrum shown in FIGURE is shown in Table 1 (1H-NMR).

TABLE 1

$^1$H-NMR assignment result

| ppm | Integrated value | Split | Assignment |
| --- | --- | --- | --- |
| 1.82~1.86 | 2H | m | c |
| 2.40~2.64 | 4H | m | a, d |
| 5.14~5.28 | 2H | m | b, h1 |
| 5.62~5.67 | 1H | d | h2 |
| 6.58~6.66 | 1H | t | g |
| 7.03~7.05 | 2H | d | e |
| 7.24~7.26 | 2H | d | f |

As a result of the assignment of 1H-NMR, each signal shown in FIGURE was confirmed to be derived from 3-hydroxy-5-(4-vinylphenyl)valeric acid unit. It was also shown that the obtained PHA contained 3-hydroxy-5-(4-vinylphenyl)valeric acid unit as a main constitutional unit at a content of at least 73 unit % or more. Units other than 3-hydroxy-5-(4-vinylphenyl)valeric acid unit did not contain aromatic rings (benzene rings), and was considered to be 3-hydroxyalkanoic acid unit represented by chemical formula (2).

Example 2

Using M9 medium containing 5-(4-vinylphenyl)valeric acid and glucose as a carbon source, strain YN2 was cultured by two-step culture for PHA production.

A colony of strain YN2 grown on an agar plate was inoculated in a 500 ml shaking flask containing 200 ml of M9 medium containing 0.5% of glucose and 0.05% of 5-(4-vinylphenyl)valeric acid and cultured at 30° C. for 48 hours. After that, the grown cells were collected by centrifugal separation.

Then the collected cells were transferred in a 500 ml shaking flask containing 200 ml of M9 culture medium containing 0.5% of glucose and 0.05% of 5-(4-vinylphenyl) valeric acid but not $NH_4Cl$ and cultured at 30° C. for 48 hours. After that, the grown cells were collected by centrifugal separation and washed with methanol and lyophilized. The dry cell matter was weighed.

Chloroform was added to the dried cells to extract the polymer at 40° C. for 24 hours. The chloroform extract was filtered to remove cell debris and the chloroform layer in which the polymer had been dissolved was concentrated by an evaporator. Then the residue was recovered with cold methanol. The recovered precipitate was then dried under reduced pressure to obtain an objective polymer. The dry cell weight was 203 mg and the weight of the obtained (recovered) polymer was 17 mg.

The average molecular weight of the obtained polymer was measured by gel permeation chromatography (GPC) (HLC-8220 GPC; Toso Co., Ltd., Column: TSK-GEL Super HM-H; Toso Co., Ltd., Solvent: chloroform, polystyrene standards). As a result, the obtained polymer had a number-average molecular weight: $Mn=8100$ and a weight-average molecular weigh: $Mw=17000$.

The structure of the obtained polymer was determined by 1H-NMR (FT-NMR: Bruker DPX400; resonance frequency: 400 MHz; measurement nuclide: 1H; used solvent: CDC13; reference: capillary enclosed TMS/CDC13; measurement temperature: room temperature). As a result, a spectrum corresponding to 1H-NMR signals in Example 1 was observed and was confirmed that PHA contained 3-hydroxy-5-(4-vinylphenyl)valeric acid unit as the main constitutional unit and from the strength of the spectrum, at 97 unit % or more.

Example 3

Using M9 medium containing 5-(4-vinylphenyl)valeric acid and sodium pyruvate as an organic acid, strain YN2 was cultured by two-step culture for PHA production.

Cell culture and PHA production was carried out in the same manner as in Example 2, except that glucose was replaced with sodium pyruvate being an alpha oxocarboxylic acid in the glycolytic or gluconeogenetic pathway. The dried cells were weighed and the polymer was recovered by the same procedure and conditions. The weight of the dried cells was 145 mg and the weight of the obtained polymer (the amount recovered) was 29 mg.

The average molecular weight of the obtained polymer was measured by gel permeation chromatography (GPC) (HLC-8220 GPC; Toso Co., Ltd., Column: TSK-GEL Super HM-H; Toso Co., Ltd., Solvent: chloroform, polystyrene standards). As a result, the obtained polymer had the number-average molecular weight: $Mn=7300$ and the weight-average molecular weight: $Mw=16000$.

The structure of the obtained polymer was determined with 1H-NMR (FT-NMR: Bruker DPX400; resonance frequency: 400 MHz; measurement nuclide: 1H; used solvent: CDC13; reference: capillary enclosed TMS/CDC13; measurement temperature: room temperature). As a result, a spectrum corresponding to 1H-NMR signal described in the above described Example 1 was observed and was confirmed that it indicated PHA having 3-hydroxy-5-(4-vinylphenyl)valeric acid unit as the main constitutional unit. From the strength of the spectrum, the content of 3-hydroxy-5-(4-vinylphenyl)valeric acid unit was at least 99 unit % or more.

Example 4

Using M9 medium containing 5-(4-vinylphenyl)valeric acid and polypeptone as a peptide source, strain YN2 was cultured by one-step culture for PHA production. PHA was extracted with acetone as well as chloroform.

A colony of strain YN2 grown on an agar plate was inoculated in a 500 ml shaking flask containing 200 ml of M9 culture medium containing 0.5% of polypeptone and 0.05% of 5-(4-vinylphenyl)valeric acid and cultured at 30° C. for 72 hours. After that, the grown cells were collected by centrifugal separation and washed with methanol and lyophilized. The dry cell matter was weighed.

Chloroform was added to the dried cells to extract the polymer at 25° C. for 72 hours. The chloroform extract was filtered to remove cell debris and the chloroform layer in which the polymer had been dissolved was concentrated by an evaporator. Then the residue was dissolved with acetone and the insoluble matter was removed by filtration. The acetone extract was concentrated by an evaporator and precipitated with cold methanol. The recovered precipitate was then dried under reduced pressure to obtain an objective polymer. The dry cell weight was 155 mg and the weight of the obtained (recovered) polymer was 20 mg.

The average molecular weight of the obtained polymer was measured by gel permeation chromatography (HLC-8220 GPC; Toso Co., Ltd., Column: TSK-GEL Super HM-H; Toso Co., Ltd., Solvent: chloroform, polystyrene standards). As a result, the obtained polymer had the number-average molecular weight: $Mn=9900$ and the weight-average molecular weight: $Mw=39000$.

The structure of the obtained polymer was determined by 1H-NMR (FT-NMR: Bruker DPX400; resonance frequency: 400 MHz; measurement nuclide: 1H; used solvent: CDC13; reference: capillary enclosed TMS/CDC13; measurement temperature: room temperature). As a result, a spectrum corresponding to 1H-NMR signal described in the above described Example 1 was observed and was confirmed that it indicated PHA having 3-hydroxy-5-(4-vinylphenyl) valeric acid unit as the main constitutional unit. From the strength of the spectrum, the content of 3-hydroxy-5-(4-vinylphenyl)valeric acid unit was at least 99 unit % or more.

Example 5

Using M9 medium containing 5-(4-vinylphenyl)valeric acid and yeast extract, strain P161 was cultured by one-step culture for PHA production. PHA was extracted with acetone as well as chloroform.

A colony of strain P161 grown on an agar plate was inoculated in a 500 ml shaking flask containing 200 ml of M9 culture medium containing 0.5% of yeast extract and 0.05% of 5-(4-vinylphenyl)valeric acid and cultured at 30° C. for 72 hours. After that, the grown cells were collected by centrifugal separation and washed with methanol and lyophilized. The dry cell matter was weighed.

Chloroform was added to the dried cells to extract the polymer at 25° C. for 72 hours. The chloroform extract was filtered to remove cell debris and the chloroform layer in which the polymer had been dissolved was concentrated by an evaporator. Then the residue was dissolved with acetone and the insoluble matter was removed by filtration. The acetone extract was concentrated by an evaporator and precipitated with cold methanol. The recovered precipitate was then dried under reduced pressure to obtain an objective polymer. The dry cell weight was 135 mg and the weight of the obtained (recovered) polymer was 16 mg.

The average molecular weight of the obtained polymer was measured by gel permeation chromatography (HLC-8220 GPC; Toso Co., Ltd., Column: TSK-GEL Super HM-H; Toso Co., Ltd., Solvent: chloroform, polystyrene standards). As a result, the obtained polymer had the number-average molecular weight: Mn=8900 and the weight-average molecular weight: Mw=32000.

The structure of the obtained polymer was determined by 1H-NMR (FT-NMR: Bruker DPX400; resonance frequency: 400 MHz; measurement nuclide: 1H; used solvent: CDC13; reference: capillary enclosed TMS/CDC13; measurement temperature: room temperature). As a result, a spectrum corresponding to 1H-NMR signal described in the above described Example 1 was observed and was confirmed that it indicated PHA having 3-hydroxy-5-(4-vinylphenyl) valeric acid unit as the main constitutional unit. From the strength of the spectrum, the content of 3-hydroxy-5-(4-vinylphenyl)valeric acid unit was at least 99 unit % or more.

Example 6

Using M9 medium containing 5-(4-vinylphenyl)valeric acid and yeast extract, strain H45 was cultured by one-step culture for PHA production. PHA was extracted with acetone as well as chloroform.

A colony of strain H45 grown on an agar plate was inoculated in a 500 ml shaking flask containing 200 ml of M9 culture medium containing 0.5% of yeast extract and 0.05% of 5-(4-vinylphenyl)valeric acid and cultured at 30° C. for 72 hours. After that, the grown cells were collected by centrifugal separation and washed with methanol and lyophilized. The dry cell matter was weighed.

Chloroform was added to the dried cells to extract the polymer at 25° C. for 72 hours. The chloroform extract was filtered to remove cell debris and the chloroform layer in which the polymer had been dissolved was concentrated by an evaporator. Then the residue was dissolved with acetone and the insoluble matter was removed by filtration. The acetone extract was concentrated by an evaporator and precipitated with cold methanol. The recovered precipitate was then dried under reduced pressure to obtain an objective polymer. The dry cell weight was 135 mg and the weight of the obtained (recovered) polymer was 16 mg.

The average molecular weight of the obtained polymer was measured by gel permeation chromatography (HLC-8220 GPC; Toso Co., Ltd., Column: TSK-GEL Super HM-H; Toso Co., Ltd., Solvent: chloroform, polystyrene standards). As a result, the obtained polymer had the number-average molecular weight: Mn=8900 and the weight-average molecular weight: Mw=32000.

The structure of the obtained polymer was determined by 1H-NMR (FT-NMR: Bruker DPX400; resonance frequency: 400 MHz; measurement nuclide: 1H; used solvent: CDC13; reference: capillary enclosed TMS/CDC13; measurement temperature: room temperature). As a result, a spectrum corresponding to 1H-NMR signal described in the above described Example 1 was observed and was confirmed that it indicated PHA having 3-hydroxy-5-(4-vinylphenyl) valeric acid unit as the main constitutional unit. From the strength of the spectrum, the content of 3-hydroxy-5-(4-vinylphenyl)valeric acid unit was at least 99 unit % or more.

Example 7

Using M9 medium containing 5-(4-vinylphenyl)valeric acid and yeast extract, strain P91 was cultured by one-step culture for PHA production. PHA was extracted with acetone as well as chloroform.

A colony of strain P91 grown on an agar plate was inoculated in a 500 ml shaking flask containing 200 ml of M9 culture medium containing 0.5% of yeast extract and 0.05% of 5-(4-vinylphenyl)valeric acid and cultured at 30° C. for 96 hours. After that, the grown cells were collected by centrifugal separation and washed with methanol and lyophilized. The dry cell matter was weighed.

Chloroform was added to the dried cells to extract the polymer at 25° C. for 72 hours. The chloroform extract was filtered to remove cell debris and the chloroform layer in which the polymer had been dissolved was concentrated by an evaporator. Then the residue was dissolved with acetone and the insoluble matter was removed by filtration. The acetone extract was concentrated by an evaporator and precipitated with cold methanol. The recovered precipitate was then dried under reduced pressure to obtain an objective polymer. The dry cell weight was 105 mg and the weight of the obtained (recovered) polymer was 11 mg.

The average molecular weight of the obtained polymer was measured by gel permeation chromatography (HLC-8220 GPC; Toso Co., Ltd., Column: TSK-GEL Super HM-H; Toso Co., Ltd., Solvent: chloroform, polystyrene standards). As a result, the obtained polymer had the number-average molecular weight: Mn=9200 and the weight-average molecular weight: Mw=31000.

The structure of the obtained polymer was determined by 1H-NMR (FT-NMR: Bruker DPX400; resonance frequency: 400 MHz; measurement nuclide: 1H; used solvent: CDC13; reference: capillary enclosed TMS/CDC13; measurement temperature: room temperature). As a result, a spectrum corresponding to 1H-NMR signal described in the above described Example 1 was observed and was confirmed that it indicated PHA having 3-hydroxy-5-(4-vinylphenyl) valeric acid unit as the main constitutional unit. From the strength of the spectrum, the content of 3-hydroxy-5-(4-vinylphenyl)valeric acid unit was at least 99 unit % or more.

Example 8

Using M9 medium containing 8-(4-vinylphenyl)octanoic acid and polypeptone, strain YN2 was cultured by one-step culture for PHA production. PHA was extracted with acetone as well as chloroform.

A colony of strain YN2 grown on an agar plate was inoculated in a 500 ml shaking flask containing 200 ml of M9 culture medium containing 0.5% of polypeptone and 0.05% of 8-(4-vinylphenyl)octanoic acid and cultured at 30° C. for 96 hours. After that, the grown cells were collected by centrifugal separation and washed with methanol and lyophilized. The dry cell matter was weighed.

Chloroform was added to the dried cells to extract the polymer at 25° C. for 72 hours. The chloroform extract was filtered to remove cell debris and the chloroform layer in which the polymer had been dissolved was concentrated by an evaporator. Then the residue was dissolved with acetone and the insoluble matter was removed by filtration. The acetone extract was concentrated by an evaporator and precipitated with cold methanol. The recovered precipitate was then dried under reduced pressure to obtain an objective polymer. The dry cell weight was 170 mg and the weight of the obtained (recovered) polymer was 26 mg.

The average molecular weight of the obtained polymer was measured by gel permeation chromatography (HLC-8220 GPC; Toso Co., Ltd., Column: TSK-GEL Super HM-H; Toso Co., Ltd., Solvent: chloroform, polystyrene standards). As a result, the obtained polymer had the number-average molecular weight: Mn=12000 and the weight-average molecular weight: Mw=38000.

The structure of the obtained polymer was determined by 1H-NMR (FT-NMR: Bruker DPX400; resonance frequency:

400 MHz; measurement nuclide: 1H; used solvent: CDC13; reference: capillary enclosed TMS/CDC13; measurement temperature: room temperature). As a result, it was shown that the polymer was PHA containing 3-hydroxy-8-(4-vinylphenyl)octanoic acid units represented by the following chemical formula (7) and 3-hydroxy-6-(4-vinylphenyl)hexanoic acid units represented by chemical formula (8) in the ratio of 30:70.

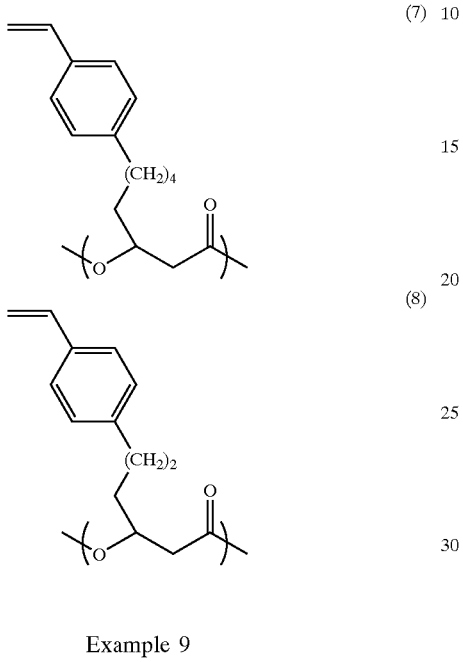

Example 9

Using M9 medium containing 10-(4-vinylphenyl)decanoic acid and polypeptone, strain YN2 was cultured by one-step culture for PHA production. PHA was extracted with acetone as well as chloroform.

A colony of strain YN2 grown on an agar plate was inoculated in a 500 ml shaking flask containing 200 ml of M9 culture medium containing 0.5% of polypeptone and 0.05% of 10-(4-vinylphenyl)decanoic acid and cultured at 30° C. for 96 hours. After that, the grown cells were collected by centrifugal separation and washed with methanol and lyophilized. The dry cell matter was weighed.

Chloroform was added to the dried cells to extract the polymer at 25° C. for 72 hours. The chloroform extract was filtered to remove cell debris and the chloroform layer in which the polymer had been dissolved was concentrated by an evaporator. Then the residue was dissolved with acetone and the insoluble matter was removed by filtration. The acetone extract was concentrated by an evaporator and precipitated with cold methanol. The recovered precipitate was then dried under reduced pressure to obtain an objective polymer. The dry cell weight was 160 mg and the weight of the obtained (recovered) polymer was 23 mg.

The average molecular weight of the obtained polymer was measured by gel permeation chromatography (HLC-8220 GPC; Toso Co., Ltd., Column: TSK-GEL Super HM-H; Toso Co., Ltd., Solvent: chloroform, polystyrene standards). As a result, the obtained polymer had the number-average molecular weight: Mn=10000 and the weight-average molecular weight: Mw=36000.

The structure of the obtained polymer was determined with 1H-NMR (FT-NMR: Bruker DPX400; resonance frequency: 400 MHz; measurement nuclide: 1H; used solvent: CDC13; reference: capillary enclosed TMS/CDC13; measurement temperature: room temperature). As a result, it was shown that the polymer was PHA containing 3-hydroxy-10-(4-vinylphenyl)decanoic acid units represented by the following chemical formula (10) and 3-hydroxy-8-(4-vinylphenyl)octanoic acid unit represented by chemical formula (7) and 3-hydroxy-6-(4-vinylphenyl)hexanoic acid unit represented by chemical formula (8) in the ratio of 20:30:50.

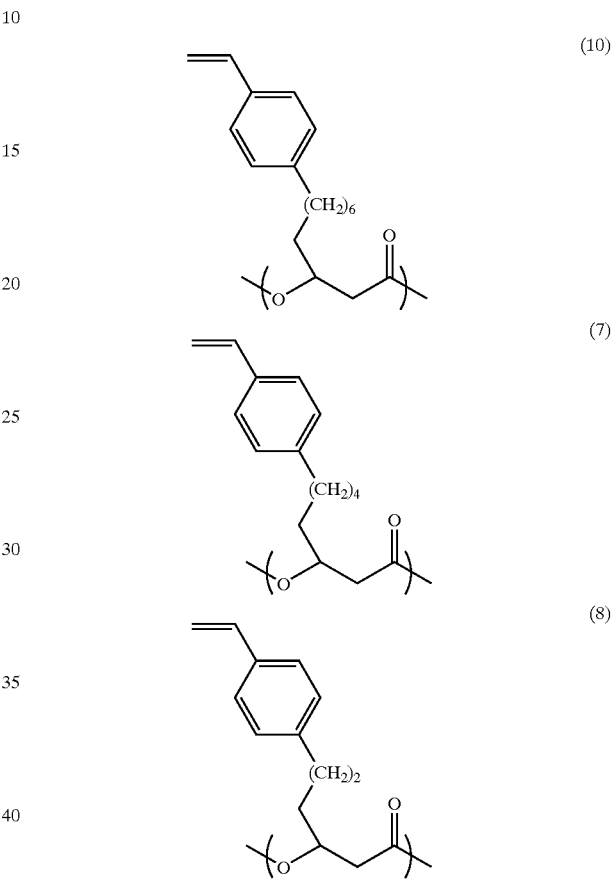

Example 10

Using M9 medium containing 11-(4-vinylphenyl)undecanoic acid and polypeptone, strain YN2 was cultured by one-step culture for PHA production. PHA was extracted with acetone as well as chloroform.

A colony of strain YN2 grown on an agar plate was inoculated in a 500 ml shaking flask containing 200 ml of M9 culture medium containing 0.5% of polypeptone and 0.05% of 11-(4-vinylphenyl)undecanoic acid and cultured at 30° C. for 120 hours. After that, the grown cells were collected by centrifugal separation and washed with methanol and lyophilized. The dry cell matter was weighed.

Chloroform was added to the dried cells to extract the polymer at 25° C. for 72 hours. The chloroform extract was filtered to remove cell debris and the chloroform layer in which the polymer had been dissolved was concentrated by an evaporator. Then the residue was dissolved with acetone and the insoluble matter was removed by filtration. The acetone extract was concentrated by an evaporator and precipitated with cold methanol. The recovered precipitate was then dried under reduced pressure to obtain an objective polymer. The dry cell weight was 170 mg and the weight of the obtained (recovered) polymer was 26 mg.

The average molecular weight of the obtained polymer was measured by gel permeation chromatography (HLC-8220 GPC; Toso Co., Ltd., Column: TSK-GEL Super HM-H; Toso Co., Ltd., Solvent: chloroform, polystyrene standards). As a result, the obtained polymer had the number-average molecular weight: Mn=11000 and the weight-average molecular weight: Mw=37000.

The structure of the obtained polymer was determined with 1H-NMR (FT-NMR: Bruker DPX400; resonance frequency: 400 MHz; measurement nuclide: 1H; used solvent: CDC13; reference: capillary enclosed TMS/CDC13; measurement temperature: room temperature). As a result, it was shown that the polymer was PHA containing 3-hydroxy-9-(4-vinylphenyl)nonanoic acid units represented by the following chemical formula (12) and 3-hydroxy-7-(4-vinylphenyl)heptanoic acid units represented by chemical formula (13) and 3-hydroxy-5-(4-vinylphenyl)valeric acid unit represented by chemical formula (3) in the ratio of 10:20:70.

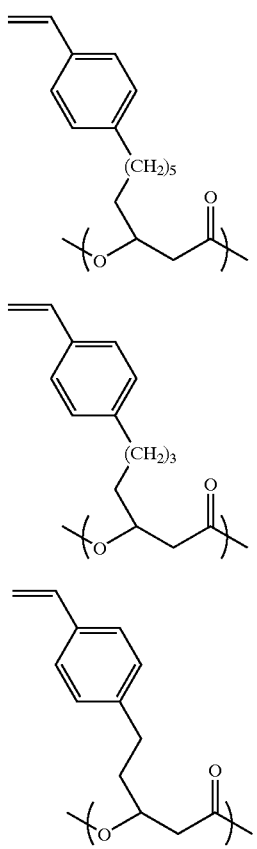

What is claimed is:

1. A polyhydroxyalkanoate type polyester comprising one unit % or more of 3-hydroxy-ω-(4-vinylphenyl)alkanoic acid unit represented by chemical formula (1):

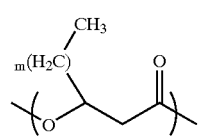

$n = 0–7$ where n is one or more integers arbitrarily selected from 0 to 7.

2. The polyester according to claim 1, wherein the polyester further comprises 3-hydroxy-alkanoic acid unit represented by chemical formula (2):

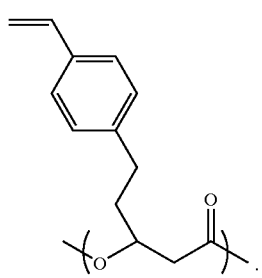

$m = 0–8$ where m is one or more integers arbitrarily selected from 0 to 8.

3. The polyester according to claim 1, wherein the polyester contains one unit % or more of 3-hydroxy-5-(4-vinylphenul)valeric acid unit represented by chemical formula (3) in the molecule, (3)

4. The polyester according to claim 1, wherein the polyester has a number-average molecular weight ranging from 3000 to 200000.

5. A method of producing a polyester comprising the steps of:
   (1) providing ω-(4-vinylphenyl)alkanoic acid represented by chemical formula (4) as a raw material,

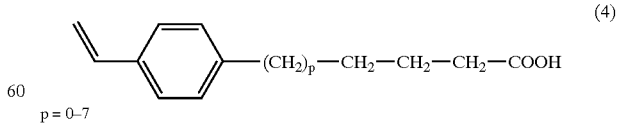

$p = 0–7$ where p is one or more integers arbitrarily selected from 0 to 7; and
   (2) producing a polyester comprising one unit % or more of 3-hydroxy-ω-(4-vinylphenyl)alkanoic acid unit represented by chemical formula (1) by using a microorganism capable of producing the polyester from the ω-(4-vinylphenyl)alkanoic acid,

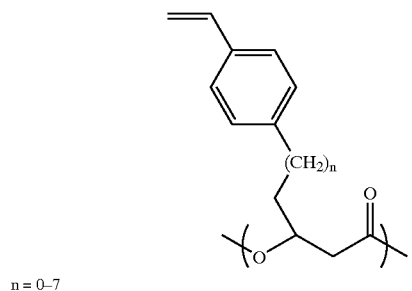

(1)

n = 0–7 where n is one or more integers arbitrarily selected from 0 to 7.

6. The method according to claim 5, wherein the step (2) comprises the step (3) of culturing the microorganism in a culture medium containing the ω-(4-vinylphenyl)alkanoic acid.

7. The method according to claim 5, wherein the ω-(4-vinylphenyl)alkanoic acid is 5-(4-vinylphenyl)valeric acid represented by chemical formula (5),

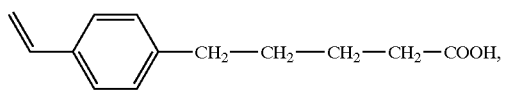

(5)

and the polyester contains one unit % or more of 3-hydroxy-5-(4-vinylphenyl)valeric acid unit represented by chemical formula (3) in the molecule,

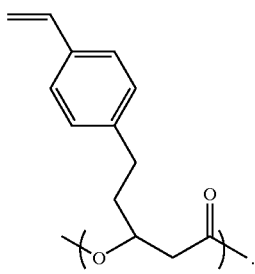

(3)

8. The method according to claim 6, wherein the culture medium contains a peptide source in addition to the ω-(4-vinylphenyl)alkanoic acid.

9. The method according to claim 8, wherein the peptide source is polypeptone.

10. The method according to claim 6, wherein the culture medium contains yeast extract in addition to the ω-(4-vinylphenyl)alkanoic acid.

11. The method according to claim 6, wherein the culture medium contains an organic acid or its salt in addition to the ω-(4-vinylphenyl)alkanoic acid.

12. The method according to claim 11, wherein the organic acid or its salt is selected from the group consisting of pyruvic acid, oxalacetic acid, citric acid, isocitric acid, ketoglutaric acid, succinic acid, fumaric acid, malic acid, lactic acid and a salt thereof.

13. The method according to claim 6, wherein the culture medium contains an amino acid or its salt in addition to the ω-(4-vinylphenyl)alkanoic acid.

14. The method according to claim 13, wherein the amino acid or its salt is selected from the group consisting of glutamic acid, aspartic acid and a salt thereof.

15. The method according to claim 6, wherein the culture medium contains a carbohydrate in addition to the ω-(4-vinylphenyl)alkanoic acid.

16. The method according to claim 15, wherein the carbohydrate is selected from the group consisting of glyceraldehyde, erythrose, arabinose, xylose, glucose, galactose, mannose, fructose, glycerol, erythritol, xylitol, gluconic acid, glucuronic acid, galacturonic acid, maltose, sucrose and lactose.

17. The method according to claim 6, wherein the culture medium contains a straight chain alkanoic acid having 4 to 12 carbon atoms or its salt in addition to the ω-(4-vinylphenyl)alkanoic acid.

18. The method of according to claim 6, wherein the step (2) further comprises the step (4) of recovering from the microorganism the polyester produced by the microorganism.

19. The method according to claim 5, wherein the microorganism belongs to genus *Pseudomonas*.

20. The method according to claim 19, wherein the microorganism is selected from the group consisting of *Pseudomonas cichorii* YN2, FERM BP-7375, *Pseudomonas cichorii* H45, FERM BP-7374, *Pseudomonas jessenii* P161, FERM BP-7376, and *Pseudomonas putida* P91, FERM BP-7373.

* * * * *

UNITED STATES PATENT AND TRADEMARK OFFICE
CERTIFICATE OF CORRECTION

PATENT NO.    : 6,803,444 B2
DATED         : October 12, 2004
INVENTOR(S)   : Suzuki et al.

It is certified that error appears in the above-identified patent and that said Letters Patent is hereby corrected as shown below:

Title page,
Item [56], References Cited, OTHER PUBLICATIONS,
"Curley, J.M., et al.," reference, "Production of Poly(3-hydroxyalkanoates) Containing Aromatic Substituents by *Pseudomonas oleovorans*", Macromolecules, vol. 29, No. 5, pp. 1726-1766 (1996)." should be deleted.
"Kim et al.;" reference, after "Kim,", "olevorans" should read -- oleovorans --.
"Lee et al.," reference, after "Lee,", "pendent" should read -- pendant --.

Column 1,
Line 35, "to the" should read -- on the --.

Column 9,
Lines 36 and 38, "PERM" should read -- FERM --.
Line 44, "patent" should read -- Patent --.

Column 13,
Line 22, "weigh:" should read -- weight: --.

Column 20,
Lines 1-12, formula (1) should read --

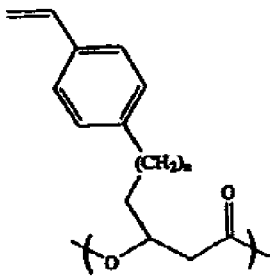

--.

UNITED STATES PATENT AND TRADEMARK OFFICE
CERTIFICATE OF CORRECTION

PATENT NO. : 6,803,444 B2
DATED : October 12, 2004
INVENTOR(S) : Suzuki et al.

It is certified that error appears in the above-identified patent and that said Letters Patent is hereby corrected as shown below:

Column 20 (cont'd),
Line 33, "vinylphenul)" should read -- vinylphenyl) --.

Signed and Sealed this

Fourteenth Day of June, 2005

JON W. DUDAS
*Director of the United States Patent and Trademark Office*